United States Patent
Maltezos et al.

(10) Patent No.: US 8,986,542 B2
(45) Date of Patent: Mar. 24, 2015

(54) MICROFLUIDIC SEPARATION DEVICE AND METHOD OF MAKING SAME

(75) Inventors: George Maltezos, Oceanside, CA (US); Alvaro Gomez, Pasadena, CA (US); Frank Gomez, Montebello, CA (US); Axel Scherer, Laguna Beach, CA (US)

(73) Assignee: California Institute of Technology, Pasadena, CA (US)

( * ) Notice: Subject to any disclaimer, the term of this patent is extended or adjusted under 35 U.S.C. 154(b) by 1916 days.

(21) Appl. No.: 12/028,773

(22) Filed: Feb. 8, 2008

(65) Prior Publication Data
US 2008/0190830 A1      Aug. 14, 2008

Related U.S. Application Data

(60) Provisional application No. 60/900,425, filed on Feb. 9, 2007.

(51) Int. Cl.
*G01N 30/60*      (2006.01)

(52) U.S. Cl.
CPC .......... *G01N 30/6095* (2013.01); *G01N 30/603* (2013.01)
USPC ....................................... 210/198.2; 210/656

(58) Field of Classification Search
CPC ................. G01N 30/6095; G01N 30/603
USPC ................... 210/635, 656, 198.2, 502.1
See application file for complete search history.

(56) References Cited

U.S. PATENT DOCUMENTS

| | | | | |
|---|---|---|---|---|
| 3,692,669 A * | 9/1972 | Bauman | ........................ | 210/656 |
| 4,664,807 A * | 5/1987 | Van Dam et al. | ............. | 210/635 |
| 5,453,163 A * | 9/1995 | Yan | ................................ | 204/451 |
| 5,858,243 A * | 1/1999 | Bedard | ......................... | 210/682 |
| 7,153,421 B2 * | 12/2006 | Koehler et al. | ............ | 210/198.2 |
| 7,261,812 B1 * | 8/2007 | Karp et al. | ................. | 210/198.2 |
| 7,514,000 B2 * | 4/2009 | Gilbert et al. | ................. | 210/635 |
| 7,790,040 B2 * | 9/2010 | Mierendorf et al. | ......... | 210/659 |
| 2002/0005383 A1 * | 1/2002 | Voute et al. | .................... | 210/656 |
| 2002/0139751 A1 * | 10/2002 | Zhang et al. | .................. | 210/656 |
| 2003/0217923 A1 * | 11/2003 | Harrison et al. | .............. | 204/450 |
| 2005/0051489 A1 * | 3/2005 | Tai et al. | ....................... | 210/656 |
| 2006/0204699 A1 | 9/2006 | Maltezos et al. | | |
| 2006/0288708 A1 | 12/2006 | Maltezos et al. | | |
| 2007/0012891 A1 | 1/2007 | Maltezos et al. | | |
| 2007/0075010 A1 * | 4/2007 | Gilbert et al. | .............. | 210/321.6 |
| 2008/0053901 A1 * | 3/2008 | Mierendorf et al. | .......... | 210/635 |
| 2008/0083465 A1 | 4/2008 | Maltezos et al. | | |

OTHER PUBLICATIONS

Wei Gu et al., Computerized microfluidic cell culture using elastomeric channels and Braille displays, Nov. 9, 2004, vol. 101, No. 45, pp. 15861 to 15866.
Po Ki Yuen et al., Semi-disposable microvalves for use with microfabricated devices or microchips, Apr. 4, 2000, pp. 401-409.

* cited by examiner

*Primary Examiner* — Ernest G Therkorn
(74) *Attorney, Agent, or Firm* — Steinfl & Bruno, LLP (57) ABSTRACT

A device and method for making a microfluidic separation device. A microfluidic separation device could include a microfluidic column having an inlet, the microfluidic column being configured to hold a first fluid and the microfluidic column including a porous portion, and an outlet attached to the microfluidic column, the outlet being configured to output a second fluid. The method may include providing a microfluidic column having an inlet, configuring the microfluidic column to hold a first fluid, forming a porous portion in the microfluidic column, and attaching an outlet to the microfluidic column.

9 Claims, 9 Drawing Sheets

MICROFLUIDIC SEPARATION DEVICE AND METHOD OF MAKING SAME

CROSS-REFERENCE TO RELATED APPLICATIONS

This application claims priority to U.S. Provisional Application No. 60/900,425; filed Feb. 9, 2007, titled "Microfluidic Three-Dimensional Separation Column."

STATEMENT REGARDING FEDERALLY SPONSORED RESEARCH OR DEVELOPMENT

The U.S. government has certain rights in this invention pursuant to Grant No. HR0011-04-1-0032 awarded by DARPA.

INCORPORATION BY REFERENCE

References cited within this application, including patents, published patent applications other publications, such as listed below:
U.S. Provisional Application No. 60/900,425; filed Feb. 9, 2007, are hereby incorporated by reference in their entirety.

THE NAMES OF THE PARTIES TO A JOINT RESEARCH AGREEMENT

California Institute of Technology, Pasadena, Calif., and California State University, Los Angeles, Calif., joined under the CSEM (Center for the Science & Engineering of Materials @ Caltech) program.

BACKGROUND

1. Field

This disclosure is generally related to a separation column and in particular to a microfluidic separation column.

2. Description of Related Art

Typically, flash column chromatography is an existing separation and/or a purification technique for use in synthetic organic and inorganic chemistry laboratories for isolating newly-synthesized materials. Generally, a column is filled with silica or a similar solid (a solid adsorbent), to create a "stationary phase." Such a column is termed a "packed column." A liquid is added to a top end of the column to create a "mobile phase." The mixture of chemicals to be separated is subsequently introduced under a pressure into the top end of the column where an equilibrium is established between a solute adsorbed and a solvent eluted flowing down the column.

Generally, in column chromatography, molecules travel under gravity through a gel (as the stationary phase) and a solvent (as the mobile phase). The solvent is one in which the materials to be separated are miscible. Different solutes will flow at different speeds, allowing for the solutes to be separated.

A chromatographic separation process is based on the difference in the surface interactions of a chemical to be analyzed and eluent molecules. A molecule with a stronger surface interaction will "sit" on the adsorbent for a longer time, will move slower, and thus get separated from another material having a weaker surface interaction which is therefore moving faster.

Existing apparatus and techniques only work with large quantities of chemicals to be separated and large volumes of liquids functioning as the mobile phase.

BRIEF SUMMARY

Embodiments of the present disclosure provide a device and method for making a microfluidic separation device. The present disclosure addresses handling of micro volumes of chemicals or specimens through the use of a miniaturized chromatographic column. This disclosure presents a means for separating micro volumes. This disclosure also presents a means for separating micro volumes using a small amount of solute as the mobile phase. This disclosure further presents the creation of a microfluidic column with a porous frit or portion which may be made of other than glass. This disclosure also presents the use of sodium silicate to make the porous portion or frit.

Briefly described, in architecture, one embodiment of the device, among others, can be implemented as follows.

A microfluidic separation device could include a microfluidic column having an inlet, the microfluidic column being configured to hold a first fluid, the microfluidic column including a porous portion. The microfluidic column may also have an outlet attached to the microfluidic column, the outlet being configured to output a second fluid.

The present disclosure can also be viewed as providing a method of making a microfluidic separation device. The method may include providing a microfluidic column having an inlet, configuring the microfluidic column to hold a first fluid, forming a porous portion in the microfluidic column. This method may also include attaching an outlet to the microfluidic column.

The methodology and device disclosed in this writing may lead to the ability to separate minute quantities of material (0.2-0.5 _L per injection). An optional integration of a microchip on top of a microfluidic column allows for manipulation of small volumes of different samples and solutions into the microfluidic column; and/or facilitating a reaction in a standard planar microfluidic microchip, wherein the reaction compounds may be separated out in a column that is bonded to the planar microfluidic microchip.

Other devices, methods, features, and advantages of what is disclosed here will be, or will become apparent, to a person having ordinary skill in the art upon examination of the following drawings and detailed description. It is intended that all such additional devices, methods, features, and advantages included within this description, be within the scope of the present disclosure, and be protected by the accompanying claims.

BRIEF DESCRIPTION OF THE VIEWS OF THE DRAWINGS

Many aspects of the disclosure can be better understood with reference to the following drawings. Components in the drawings are not necessarily to scale, emphasis instead being placed upon clearly illustrating principles of the present invention. Moreover, in the drawings, like-referenced numerals designate corresponding parts throughout the several views.

DETAILED DESCRIPTION

The present disclosure relates to a device and method for making a microfluidic separation device. In particular, the disclosure pertains to flash chromatography of micro volumes by constructing a microfluidic column capable of separating such micro volumes.

As disclosed here, a method employing flash chromatography is used. It differs from common gravity chromatography in the sense that it uses pressure to run the molecules through a packed column. In this case, using the three-dimensional "lost wax" approach for microfluidics, a method is presented for miniaturizing a chromatographic column. In the typical "lost wax" approach, a "negative" mold is made. Molten wax is injected into this mold and allowed to cool, thereby generating a wax model. The wax model is covered with plaster of Paris, for example, and heated. The heat melts the wax, which trickles out through a small hole and thus the wax is "lost," leaving a precise replica of the desired microfluidic separation column. A modification of this is here disclosed. A computer model, a structure of the device, and corresponding methods are described below.

Figure 1:
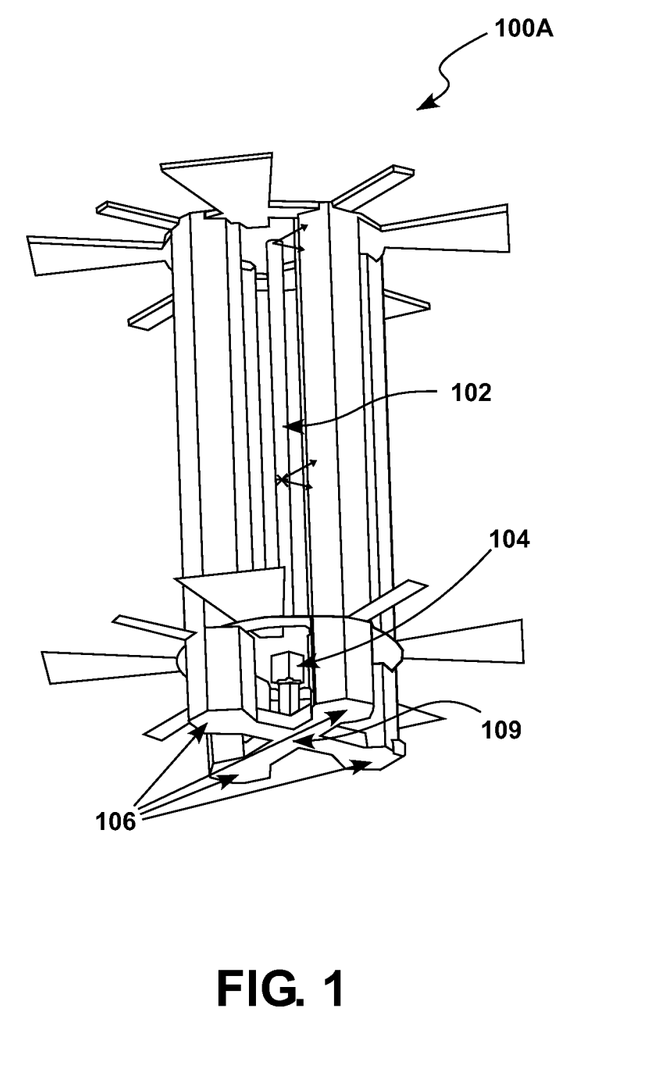
FIG. 1 illustrates a computer model of a wax structure used to make a microfluidic separation device of the present disclosure.

FIG. 1 illustrates a computer model 100A of a wax structure used to make a model of a microfluidic separation device of the present disclosure. A three-dimensional computer model 100A was first made and then realized using a rapid prototype machine, such as Solidscape T66®. The model 100A is a computer model made from the Solidworks® software, the model 100A is uploaded to a Solidscape® T66 printer, and the Solidscape® T66 printer generates a wax model. The microfluidic column described below is obtained from the wax model. The wax model may be treated as an intermediate stage between the computer model 100A and the microfluidic column.

In FIG. 1, there is seen a microfluidic column 102. Such a column may have exemplary dimensions of 600 microns in diameter and 15,000 microns in length. The dimensions may vary based on a given application. A ratio of these dimensions (preferably in a range of 1/5 to 1/40) is comparable to a very long benchtop separation column and is selected to ensure good separation of the chemicals, such as a mixture, to be passed there through. The diameter of microfluidic column 101 is of note. For example, if the diameter is too thin, that is, the diameter of microfluidic column 101 is thinner than that specified here, the microfluidic column may collapse upon construction.

In order to make such a thin vertical microfluidic column 102 of wax as shown in FIG. 1 with good reliability, it may be preferable to place one or more larger supports, such as column supports 106, around the microfluidic column 102 and a cross bar 109 as shown in FIG. 1, These may be used to secure the microfluidic column 102 during its construction or processing steps. The column supports 106 could serve as anchors for the microfluidic column 102. The column supports 106 may be used to substantially prevent the microfluidic column 102 from collapsing as the microfluidic column 102 is built by the Solidscape T66® printer. Therefore, the column supports 106 are printed together with the microfluidic column 102.

After the microfluidic column 102 is made, the column supports 106 and the cross bar 109 may be cut leaving just the microfluidic column 102. The wax made computer model 100A may include a porous portion 104, such as a "frit," a sodium silicate frit, a filter, a paper filter, glass, or a partially fused material. Other porous materials will be obvious to those skilled in the art. The inclusion of the porous portion 104 is further discussed below.

Figure 2A:
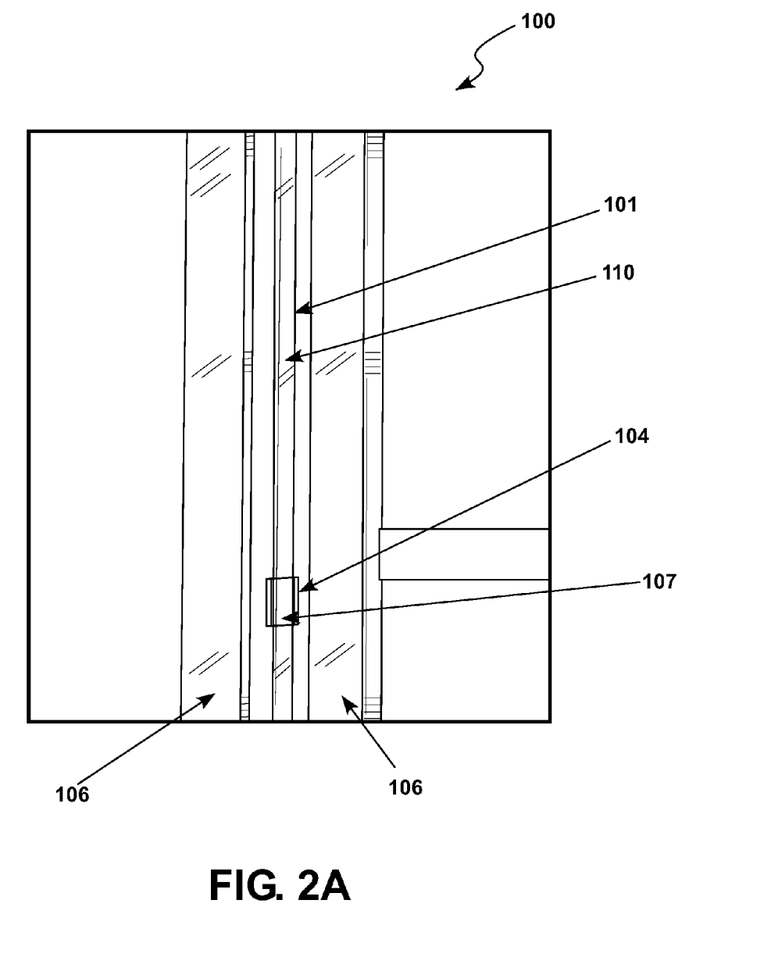
FIG. 2A illustrates a photographic view of the microfluidic separation device of the present disclosure.

Once the wax made computer model 100A is completed, it is then embedded into a poly(dimethylsiloxane) (PDMS) elastomer. The wax is then melted away to create microfluidic column 102 as seen in FIG. 2A inside the PDMS elastomer. Microfluidic column 102 has substantially the same dimensions as the wax microfluidic column 102.

FIG. 2A is a photographic view of the completed microfluidic column 101 obtained from microfluidic column 102 of FIG. 1 and cast in PDMS. A sodium silicate frit is visible at 107 and serves as the porous portion 104. The microfluidic column 101 is packed with silica 110. Traditionally, a glass frit-like material would be embedded into the microfluidic column 101 to serve as the porous portion 104 and to act as a base for the silica 110 or similar solid adsorbent which is to function as the stationary phase.

However, it is very difficult to embed a traditional glass frit into the monolithic structure of the PDMS elastomer with the necessary leak tight fit. Therefore, an alternative method was devised using sodium silicate as here presented.

Sodium silicate is liquid at room temperature. This allows construction of the porous portion 104 by placing a wire or metal pin of an appropriate diameter, for example, substantially of the same the diameter as that of the internal dimension of the microfluidic column 101, into the microfluidic column 101, up to a point in a space allocated for the porous portion 104. Leakage could be a problem if the wire or the pin is not placed at a location substantially at least one quarter the length, measured from an inlet 103 described below, of the microfluidic column 101.

As noted, the porous portion 104 is being formed in the wax mold of the microfluidic column 101. This then enables the porous portion 104 to be trapped in the polymer such that it becomes part of the microfluidic column 101 as shown in FIG. 2. for the porous portion 104. The wire or the pin is dimensioned to serve as a seal, preferably an air tight seal in the microfluidic column during formation of the porous portion 104, to hold the sodium silicate in a liquid state in the porous portion 104. In this respect, once the wire or pin is inserted to the appropriate position, sodium silicate is then injected into the microfluidic column 101 above the wire or pin and then heated at about 175 degrees Celsius for about 10 minutes or until the sodium silicate substantially crystallizes and forms a porous solid having a property for use as a frit in the microfluidic column 101. The silica 110 may then be carefully poured into the microfluidic column 101, either in dry or in a slurry form. Typically, the heating of the sodium silicate is done with a heat plate causing the sodium silicate to be substantially solidified in about 10-15 minutes. However, if the heat source used for the crystallization of the sodium silicate is a heat gun, the crystallization process is sped up and the sodium silicate may substantially crystallize in about 3 minutes.

Figure 2B:
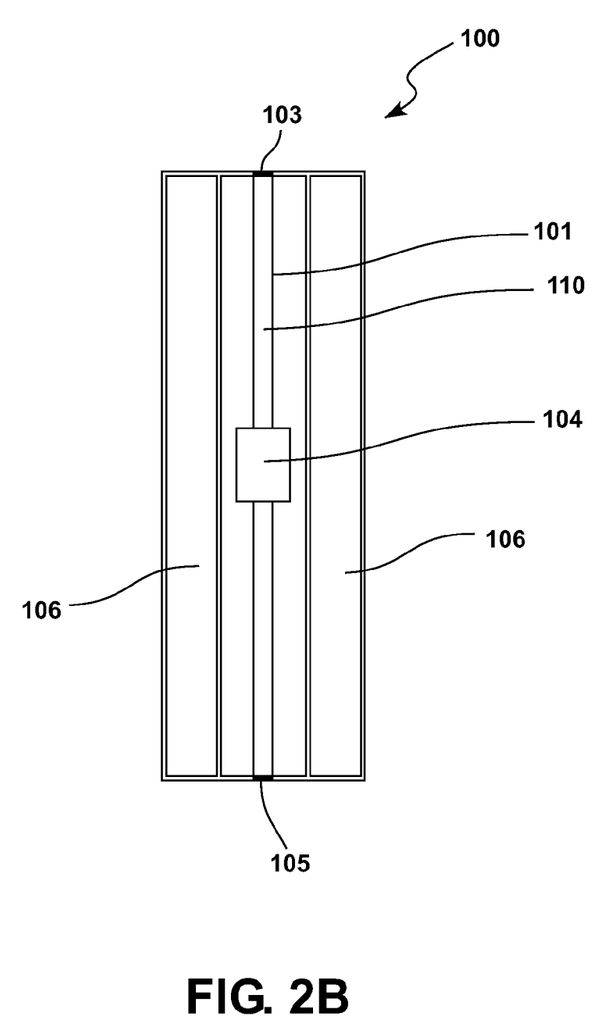
FIG. 2B illustrates a front view of the microfluidic separation device shown in FIG. 2A.

FIG. 2B illustrates a graphical representation of the photographic view of FIG. 2A which is a front view of the microfluidic separation device 100 shown in FIG. 2A. The graphical representation shows an approximate location of various features of the microfluidic separation device 100 not easily discernible in a photograph of FIG. 2A taken under a high magnification. As described above, the microfluidic separation device 100 may include a microfluidic column 101, and a porous portion 104. Further, the microfluidic column 101 may have an inlet 103, the microfluidic column 101 being configured to hold a first fluid, such as an input to be processed. Still further, an outlet 105 may be attached or defined in the microfluidic column 101, the outlet 105 being configured to output a second fluid, such as an output of a process. It may be noted that the first fluid and the second fluid may be mixed together before entering the inlet 103. That is, a second fluid may be purified or separated from a mixture of the first fluid and the second fluid.

The microfluidic column 101 may be an elution column, an affinity column or any other column that finds application in a field, such as chromatography and analytical chemistry.

In the microfluidic separation device 100 of this disclosure, the first fluid may be urged, such as under pressure transmitted by a separate object, towards the porous portion 104. The microfluidic column 101 has a length and a diameter and the length being preferably in a range of 5-40 times the diameter.

In another embodiment of the microfluidic separation device 100, the microfluidic separation device 100 may include a microfluidic column 101 having an inlet 103, the microfluidic column 101 may be configured to hold a first fluid and the microfluidic column 101 may include a porous portion 104, such as an at least partially fused material. In the microfluidic separation device 100, an outlet 105 may be attached to or defined in the microfluidic column 101, and the outlet 105 could be configured to output a second fluid, the microfluidic column 101 may be configured to process less than about 100 nanoliter to 1 milliliter of at least one of the first fluid and the second fluid. Additionally, the microfluidic column 101 may be configured to urge the first fluid towards the porous portion 104, and the microfluidic column 101 may have a length and a diameter and the length could be in a range of 5-40 times the diameter.

Figure 2C:
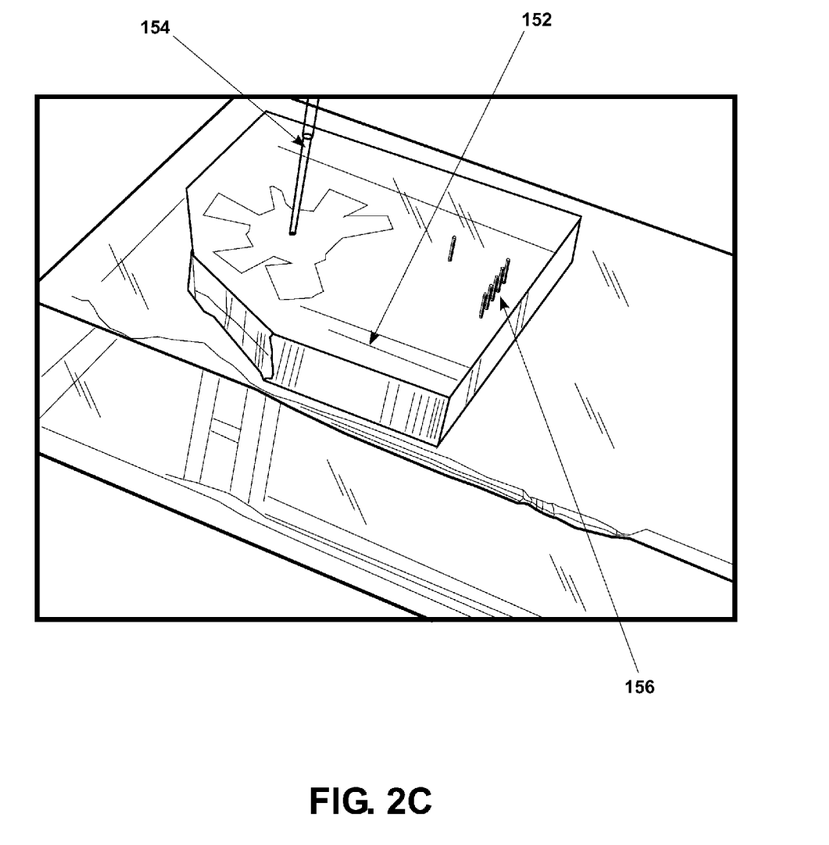
FIG. 2C illustrates a photographic view of a microchip attached to the microfluidic separation device of the present disclosure.

Now turning to the next two figures, a structure including a microchip is described. FIG. 2C illustrates a photographic view of a microchip 152 attached to the microfluidic separation device 100 of the present disclosure. A pressure transmitting element 154 and passages 156 for one or more fluids are also shown.

Figure 2D:
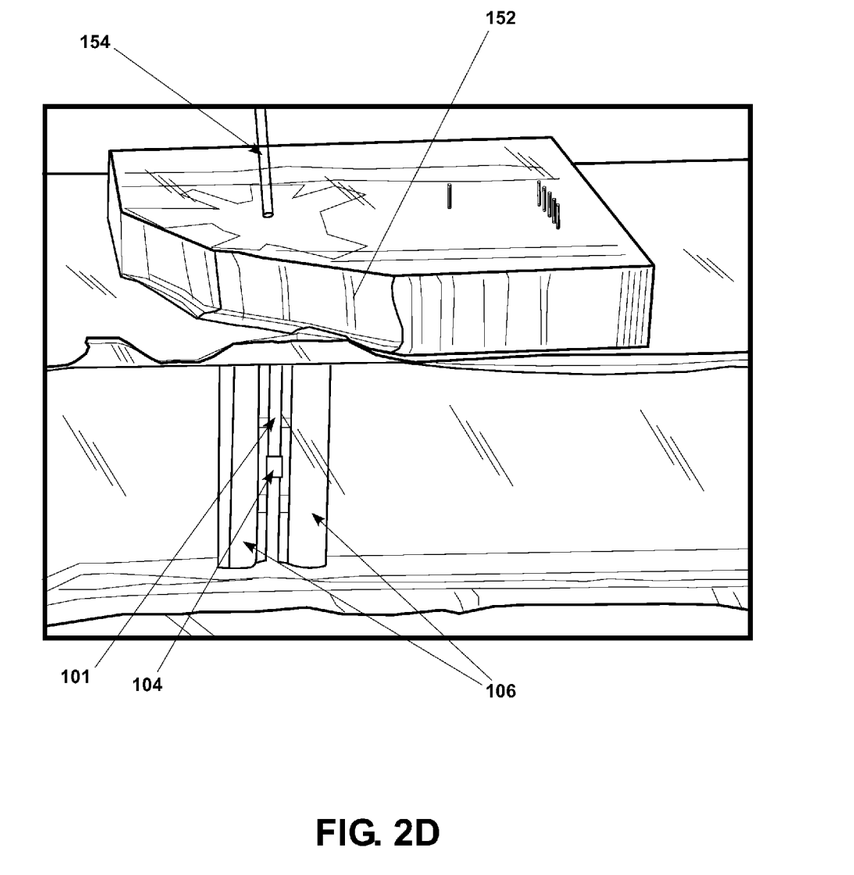
FIG. 2D illustrates a further photographic view of the microchip attached to the microfluidic separation device of the present disclosure.

FIG. 2D illustrates a further photographic view of the microchip 152 attached to the microfluidic separation device 100 of the present disclosure. This photographic view is from a different angle to show features that were not easily discernible in FIG. 2A. The pressure transmitting element 154 is shown. Further, the microfluidic column 101, the porous portion 104, and the column supports 106 are also shown.

In the context of the microchip 152, the microfluidic separation device 100 may include a plurality of microfluidic columns 101. The microchip 152, integrated on top of one or more microfluidic columns 101, may permit the manipulation of small volumes of different fluids into the microfluidic column 101 in a three-dimensional arrangement of the plurality of microfluidic columns 101. As a further example, there may be two chemicals, for example, A and B, being mixed on the microchip 152 located on top of the microfluidic column 101 where the two chemicals undergo a chemical reaction or the two chemicals are simply directed into a respective microfluidic column 101 to undergo a separation. Alternately, chemicals A and B could go into separate channels and are mixed, where a chemical reaction may occur, and reaction products may be processed into the same microfluidic column 101.

Figure 2E:
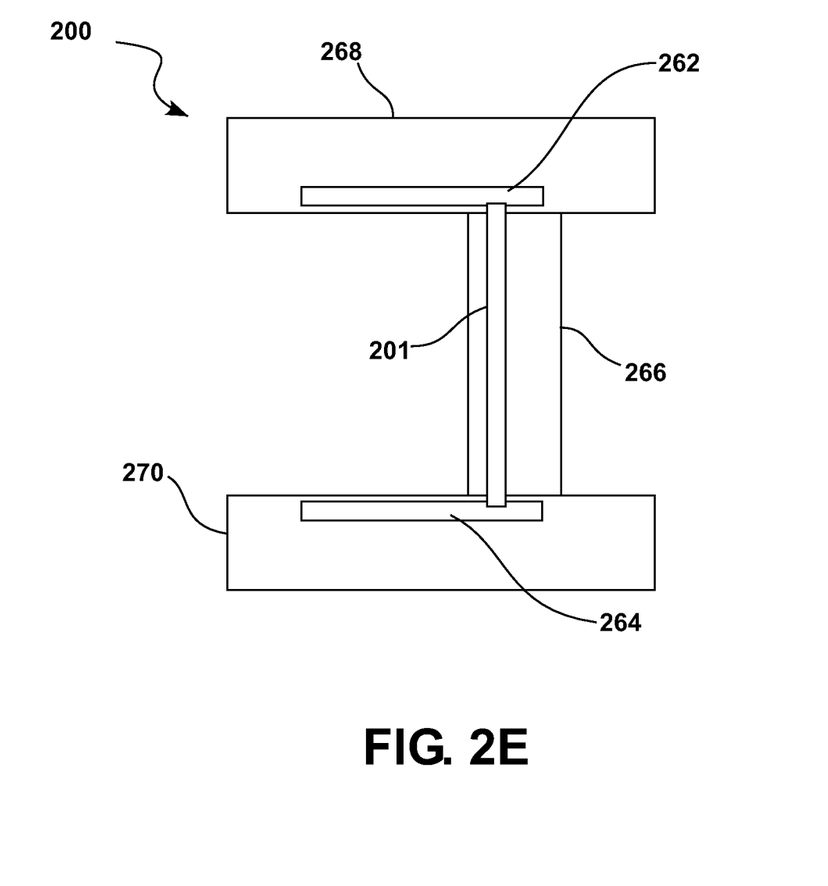
FIG. 2E illustrates a front view of a microchip, including a microfluidic channel, attached to another embodiment of the microfluidic separation device of the present disclosure.

FIG. 2E illustrates a front view of a microchip, including a microfluidic channel, attached to another embodiment of the microfluidic separation device of the present disclosure. As seen in FIG. 2E, in the microfluidic separation device 200, one or more of the microfluidic columns 201 may be connected to one or more of a first microfluidic channel 262 enclosed in a first microfluidic chip 268 and a second microfluidic channel 264 enclosed in a second microfluidic chip 270. As described earlier, a column support 266 may be included as appropriate. The microfluidic chip 270 may rest at least on top (that is, before separation of the fluid) or on the bottom (that is, after separation of the fluid) of the microfluidic separation device. In this way, one can have communication from a microfluidic channel to the microfluidic column 201 to a microfluidic channel if desired.

Figure 3A:
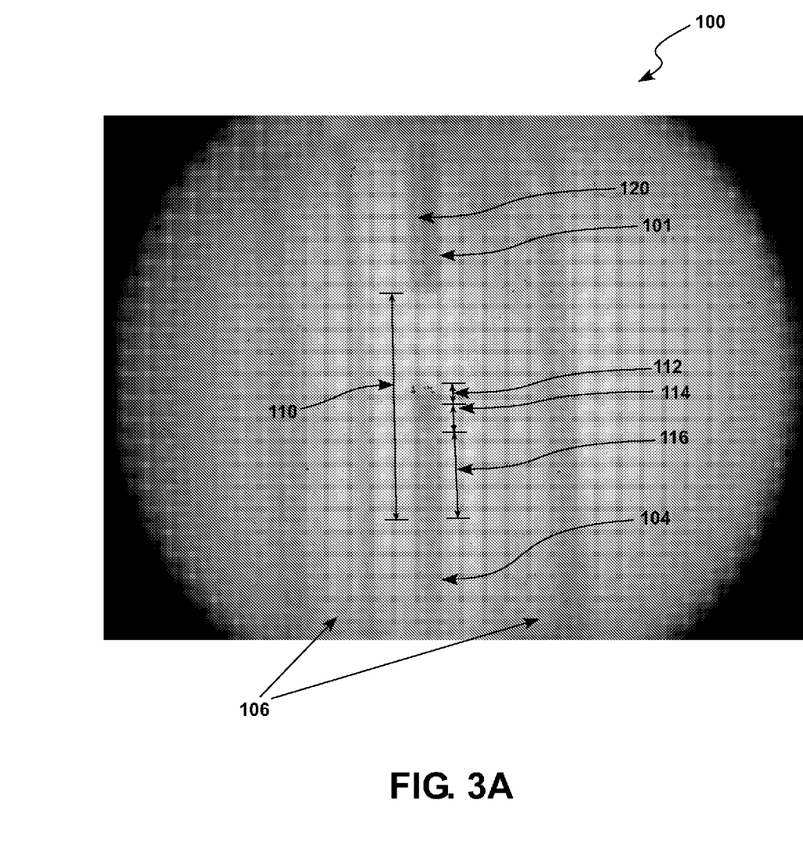
FIG. 3A illustrates a photographic view of the microfluidic separation device of the present disclosure separating a dye.

Several experiments showing a separation of fluids are described next. FIG. 3A illustrates a photographic view where a microfluidic column 101 is shown separating blue (114), green (112), and red (116) dye colors. The three bands of dye color are visible traveling down the column. FIG. 3A is shown in a graphic form as well in FIG. 3B. The microfluidic separation device 100 may include a metal cylinder 120 (typically made of Titanium) for transmitting a pressure to contents of the microfluidic separation device 100, a microfluidic column 101, a silica 110 which may further include a solvent, and a porous portion 104. Titanium may be preferred for the metal cylinder because of being non-corrosive to chemicals or organic compounds used in a typical microfluidic column 101. However, other materials may be used. Column supports 106 may also be included as shown to support the microfluidic column 101. The metal cylinder is introduced to transmit the pressure in the column to facilitate the processing of the materials to be fed through the column for separation.

In FIG. 3A, it should be noted that the silica 110 is in a portion of the microfluidic column 101 in a space between the metal cylinder 120 and the porous portion 104. A solution to be processed also occupies the space between the metal cylinder 120 and the porous portion 104. As soon as the solution comes into contact with the silica 110, which may include a solvent, a separation of constituents of the solution begins. This is because of a difference between rates of travel for molecules of constituents of the solution as known to a person having ordinary skill in the art and as discussed earlier herein. A function of the porous portion 104 is to let a liquid pass but stop a solid from passing. That is, the porous portion 104 does not let the silica 110 "drop" or pass through the porous portion 104 in order for the silica 110 to be available for the separation of the constituents of the solution, such as a green dye 112, a blue dye 114, and a red dye 116 as shown. The green dye 112, the blue dye 114, and the red dye 116 are collected at the end of the porous portion 104. The red dye 116 is followed by the blue dye 114 and the blue dye 114 is followed by the green dye 112 based on a respective traveling rate through silica 110.

Figure 3B:
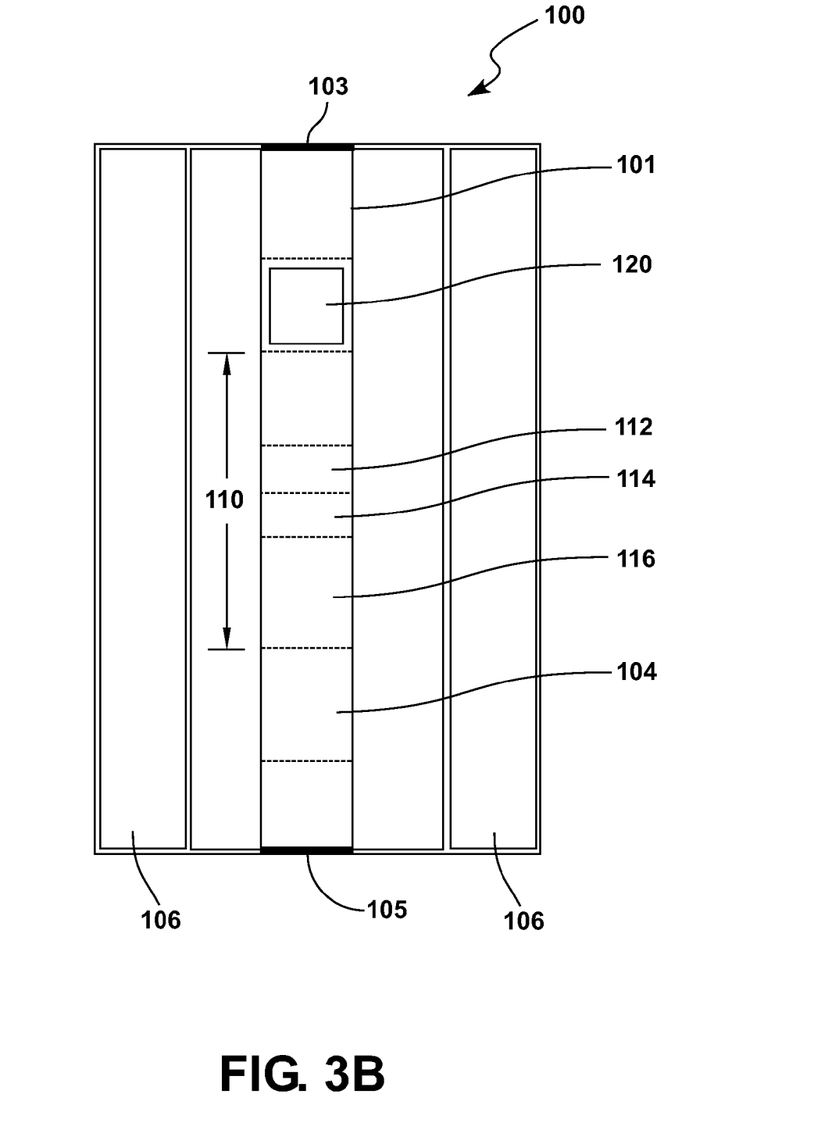
FIG. 3B illustrates a front view of the microfluidic separation device shown in FIG. 3A.

FIG. 3B illustrates a graphical representation of the photographic view of pertinent parts of FIG. 3A, which is a front view of the microfluidic separation device 100 shown in FIG. 3A. The graphical representation shows the approximate location of various features of the microfluidic separation device 100 not easily discernible in the photograph of FIG. 3A taken under a high magnification. The microfluidic separation device 100 may include an inlet 103 to the microfluidic column 101. The microfluidic column 101 may include the metal cylinder 120 to transmit a pressure to the contents of the microfluidic column 101. The microfluidic column 101 may also include the silica 110, the porous portion 104, and an outlet 105. As described above, the green dye 112, the blue dye 114, and the red dye 116 may separate as shown. In the microfluidic separation device 100, the microfluidic column 101 may be configured to process less than about 100 nanoliter to 1 milliliter of at least one of a first fluid and a second fluid.

The above description reflects an experiment in separating food dyes using the device of the present disclosure. Two food dyes were mixed and introduced into the microfluidic column 101. A pressure of 2 psi was transmitted via a 23 gauge steel pin, such as the metal cylinder 120 shown in the preceding figures, to move the two dyes through the microfluidic column 101. Typically, separation took less than about 20 minutes to be substantially complete.

In another experiment, a 0.2 _L plug of a mixture of dyes was introduced through the inlet 103 of microfluidic column 101 via a pipette. The dyes were observed to separate in the microfluidic column 101 and were collected at the outlet 105 by a suitable micro slide, for example.

The pattern of the dyes in these experiments was similar to a thin layer chromatography (TLC) done on the same dyes. Ideal conditions and solvents were not found for separating these dyes so experimental separations have been slightly "smeared." Collection is also a concern due to the fact that the microfluidic column 101 lacked a mouth initially from where the purified material may drip easily from. This was solved by using micro slides (concave slides commonly used in microbiology) attached to the bottom of the column, such as at the outlet 105, allowing the purified material to drip and be collected for further TLC plate studies.

An attempt of the microfluidic separation device 100 is to separate minute quantities of a material (0.2-0.5 _L per injection), a further attempt is to use only small volumes of the material needed for the mobile phase. These goals are potentially important for separating expensive materials and for a situation when only a small quantity of material or fluid is available. Furthermore, the microfluidic separation device 100 is portable, hence, usable both in a laboratory and in the field and easily transported between.

Figure 4:
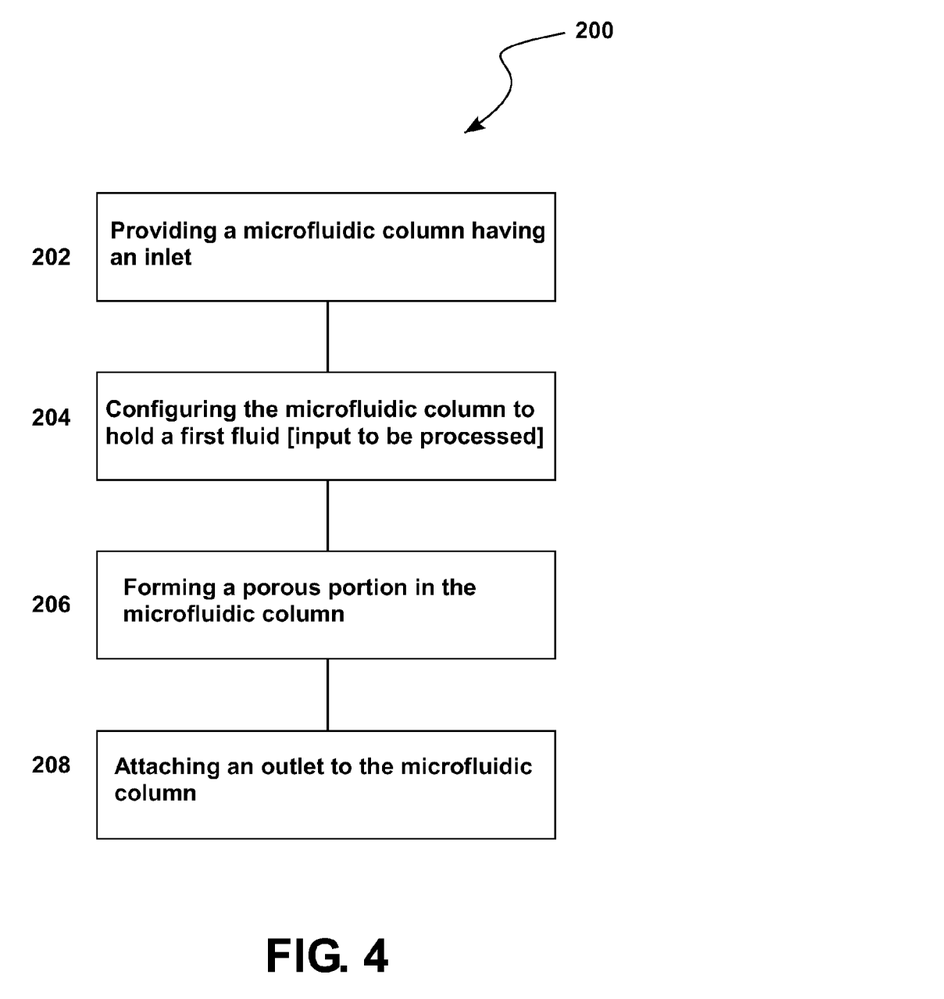
FIG. 4 is a flowchart of a method of making the microfluidic separation device of the present disclosure.

Now turning to FIG. 4, a flowchart is described for a method 200 of making the microfluidic separation device of the present disclosure. The method 200 may include providing a microfluidic column having an inlet (block 202), configuring the microfluidic column to hold a first fluid (block 204), forming a porous portion in the microfluidic column (block 206), and attaching or forming an outlet to the microfluidic column (block 208). The method 200 may further include configuring the outlet to output a second fluid. In the method 200, forming the porous portion may further be including at least a partially fused material, such as a vitreous frit, in the porous portion. Including an at least partially fused material which may further encompass including a sodium silicate.

In the method 200, when configuring the microfluidic column to hold the first fluid, such configuring could include configuring the microfluidic column to process less than 100 nanoliter to 1 milliliter, plus or minus 1%, of at least one of the first fluid and the second fluid, the second fluid passing through the outlet.

In the method 200, providing the microfluidic column may further include including a silica in the column. Providing the microfluidic column may further include providing an elution, an affinity, or a similar column.

The method 200 may further include urging the first fluid towards the porous portion. This urging may be done by any device as known to a person having ordinary skill in the art and may include vacuum or pressure or other means to move the fluid. In the method 200, the forming the porous portion may include temporarily sealing the microfluidic column at an output end of the porous portion. In the method 200, the providing the microfluidic column may include providing a microfluidic column of a material selected from: fluorinated polymer, elastomer, and plastic.

In the method 200, providing the microfluidic column may further include providing a plurality of microfluidic columns.

In the method 200, the providing the microfluidic column may further include connecting one or more of the microfluidic columns to one or more of a first microfluidic channel enclosed in a first microfluidic chip and a second microfluidic channel enclosed in a second microfluidic chip.

In a further embodiment of the method 200, the method 200 may include selecting one or more dimensions of a microfluidic column, creating a mold of the microfluidic column, forming a porous portion in the mold of the microfluidic column, embedding the mold of the microfluidic column in one of a fluorinated polymer, an elastomer, and a plastic; and removing the mold. In the further embodiment of the method 200, the method 200 may further include removing the wax.

Another embodiment of the method 200 may include: providing a microfluidic column having an inlet, configuring the microfluidic column to hold a first fluid, including a porous portion in the microfluidic column, including at least a partially fused material, such as a vitreous frit, in the porous portion, attaching or including an outlet to the microfluidic column, configuring the outlet to output a second fluid, sizing the microfluidic column to process less than about 100 nanoliter to 1 milliliter of at least one of the first fluid and the second fluid, configuring the microfluidic column to urge the first fluid towards the porous portion, and sizing the microfluidic column to have a length and a diameter, wherein the length is in a range of 5-40 times the diameter.

The foregoing method 200, or elements of the method 200, could also be stored on a computer-readable medium having computer-executable instructions to implement the method 200 or the elements of the method 200.

As a person having ordinary skill in the art would appreciate, the elements or blocks of the methods described above could take place at the same time or in an order different from the described order.

Obvious modifications to the foregoing involve using a larger number of solvents. Further, the microfluidic columns may be made in fluorinated polymers such as sifel and PFPE and to allow the majority of organic solvents to be used. Additionally a multilayer stack of two and three-dimensional microfluidics can be aligned to the columns in order to introduce fluids into the microfluidic columns and extract it afterwards. Additionally, it is quite easy to make large arrays of these columns to facilitate the possibilities for combinatorial chemistry and other applications in which multiple reactions need to be carried out and purified.

The microfluidic columns may be built in a variety of molding methods, including 2-piece and 1-piece molds where the column is formed by two pieces or even one piece wherein the column slides out after the polymer is cured. If the polymer is soft enough the piece used to create the porous portion 104 for the frit will be able to get out of an elastic material without damage to the microfluidic column, These microfluidic columns do not have to be formed by rapid prototyping and simpler molds can be used. These microfluidic columns can be built from many different types of elastomers and plastics.

As used in this specification and appended claims, the singular forms "a," "an," and "the" include plural referents unless the specification clearly indicates otherwise. The term "plurality" includes two or more referents unless the specification clearly indicates otherwise. Further, unless described otherwise, all technical and scientific terms used herein have meanings commonly understood by a person having ordinary skill in the art to which the disclosure pertains.

It should be emphasized that the above-described embodiments are merely some possible examples of implementation, set forth for a clear understanding of the principles of the disclosure. Many variations and modifications may be made to the above-described embodiments of the invention without departing substantially from the principles of the invention. All such modifications and variations are intended to be included herein within the scope of this disclosure and the present invention and protected by the following claims.

What is claimed is:

1. A microfluidic separation device comprising:
    a microfluidic column having a first section and a second section,
        the first section being a section of the microfluidic column between an inlet and a crystallized porous solid portion, and configured to hold a first fluid, and
        the second section being a section of the microfluidic column between the crystallized porous solid portion and an outlet, and configured to hold a second fluid;
    the crystallized porous solid portion being embedded and trapped within the microfluidic column, the crystallized porous solid portion fluidly separating the first section from the second section, the crystallized porous solid portion forming a monolithic structure with the microfluidic column such that the crystallized porous solid portion is monolithically part of the microfluidic column; and
    the outlet attached to the microfluidic column, the outlet being configured to output a second fluid,
    wherein the crystallized porous solid portion comprises sodium silicate.

2. The microfluidic separation device of claim 1, wherein the microfluidic column is configured to process less than a range of 100 nanoliter to 1 milliliter of at least one of the first fluid and the second fluid.

3. The microfluidic separation device of claim 1, wherein the microfluidic column includes a silica.

4. The microfluidic separation device of claim 1, wherein the microfluidic column is one of an elution column and an affinity column.

5. The microfluidic separation device of claim 1, wherein the microfluidic separation device is configured to urge the first fluid from the inlet towards the crystallized porous solid portion.

6. The microfluidic separation device of claim 1 further including a plurality of microfluidic columns.

7. The microfluidic separation device of claim 6, wherein one or more of the microfluidic columns is connected to one or more of a first microfluidic channel enclosed in a first microfluidic chip and a second microfluidic channel enclosed in a second microfluidic chip, wherein the microfluidic channel is located at least before the separation of the first fluid or after the separation of the first fluid.

8. The microfluidic separation device of claim 1 wherein the microfluidic column is configured to process less than a range of 100 nanoliter to 1 milliliter of at least one of the first fluid and the second fluid;
    the microfluidic column being configured to urge the first fluid towards the crystallized porous solid portion; and
    the microfluidic column having a length and a diameter and the length being in a range of 5-40 times the diameter.

9. A separation device comprising:
    a microfluidic column having a first section and a second section,
        the first section being a section of the microfluidic column between an inlet and a crystallized porous solid portion, and configured to hold a first fluid, and
        the second section being a section of the microfluidic column between the crystallized porous solid portion and an outlet, and configured to hold a second fluidthe microfluidic column including;
    the crystallized porous solid portion being embedded and trapped within the microfluidic column, the crystallized porous solid portion fluidly separating the first section from the second section, the crystallized porous solid portion forming a monolithic structure with the microfluidic column such that the crystallized porous solid portion is monolithically part of the microfluidic column;
    the outlet associated with the microfluidic column, the outlet being configured to output a second fluid; and
    a microfluidic circuit, the microfluidic circuit being connected to the microfluidic column either before separation of said first fluid or after separation of said first fluid,
    wherein the crystallized porous solid portion comprises sodium silicate.

* * * * *